US012102360B1

(12) United States Patent
Frock et al.

(10) Patent No.: US 12,102,360 B1
(45) Date of Patent: Oct. 1, 2024

(54) COMPRESSIBLE CERVICAL PLATE

(71) Applicant: Spinal Simplicity, LLC, Overland Park, KS (US)

(72) Inventors: Adam Frock, Lenexa, KS (US); Adam Rogers, Olathe, KS (US); Todd Moseley, Olathe, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 18/488,870

(22) Filed: Oct. 17, 2023

(51) Int. Cl.
*A61B 17/80* (2006.01)
*A61B 17/70* (2006.01)

(52) U.S. Cl.
CPC ...... *A61B 17/8004* (2013.01); *A61B 17/7044* (2013.01); *A61B 17/7059* (2013.01); *A61B 17/8042* (2013.01); *A61B 17/8047* (2013.01); *A61B 17/8057* (2013.01); *A61B 2560/02* (2013.01)

(58) Field of Classification Search
CPC .......... A61B 2017/681; A61B 17/7044; A61B 17/7059; A61B 17/80; A61B 17/8004; A61B 17/8042; A61B 17/8047; A61B 17/8057
See application file for complete search history.

(56) References Cited

U.S. PATENT DOCUMENTS

| | | | |
|---|---|---|---|
| 7,763,056 B2 * | 7/2010 | Dalton | A61B 17/7059 606/280 |
| 8,262,711 B2 | 9/2012 | Hess | |
| 8,574,270 B2 | 11/2013 | Hess et al. | |
| 8,814,915 B2 | 8/2014 | Hess et al. | |
| 8,882,812 B2 | 11/2014 | Hess et al. | |
| 8,940,029 B2 * | 1/2015 | Leung | A61B 17/8605 606/291 |
| 8,974,504 B2 * | 3/2015 | Hess | A61B 17/8028 606/282 |
| 9,095,388 B2 | 8/2015 | Hess et al. | |
| 10,092,336 B2 | 10/2018 | Hess et al. | |
| 10,485,592 B2 | 11/2019 | Moseley et al. | |

FOREIGN PATENT DOCUMENTS

| | | |
|---|---|---|
| AU | 2010223890 B2 | 11/2015 |
| AU | 2013259272 B2 | 1/2018 |
| AU | 2018202671 A1 | 5/2018 |
| CA | 2873397 A1 | 11/2013 |
| CA | 2755264 C | 10/2017 |
| CN | 104684495 A | 6/2015 |

(Continued)

OTHER PUBLICATIONS

U.S. Appl. No. 61/160,154, Mar. 13, 2009, Hess.
U.S. Appl. No. 61/688,247, May 10, 2012, Harold Hess.

*Primary Examiner* — Larry E Waggle, Jr.
(74) *Attorney, Agent, or Firm* — Erise IP, P.A.

(57) ABSTRACT

A compressible plate including a plurality of plate segments for compressing two or more osseous structures. The compressible cervical plate includes a spring retaining member extending from at least one plate segment and a spring retaining member recess disposed at another plate segment, the spring retaining member recess receiving the spring retaining member. A spring disposed at the spring retaining member and providing active compression between the plurality of plate segments.

20 Claims, 11 Drawing Sheets

(56) References Cited

FOREIGN PATENT DOCUMENTS

| | | |
|---|---|---|
| EP | 2405838 A1 | 1/2012 |
| EP | 2846721 A4 | 1/2016 |
| JP | 5548710 B2 | 7/2014 |
| JP | 6214011 B2 | 10/2017 |
| JP | 6407367 B2 | 10/2018 |
| WO | 2010105279 A1 | 9/2010 |
| WO | 2013170164 A1 | 11/2013 |

* cited by examiner

COMPRESSIBLE CERVICAL PLATE

BACKGROUND

1. Field

The present disclosure relates to implantable orthopedic appliances. Particularly, the present disclosure is directed to a compression plate system for use in supporting a section of the vertebral column.

2. Related Art

A variety of implantable orthopedic devices are known in the art for assisting recovery following trauma or injury. Of such devices, many are directed to relatively rigid devices that force substantial load transfer from the anatomical structure to the orthopedic device, for example, from the vertebral column to the implanted cervical plate. In some circumstances, such load transfer inhibits desirable loading of the anatomical structure. In the case of osseous tissue, insufficient loading will inhibit, reduce, or prevent ossification of the structure, the concept of which is described by and known as "Wolff's Law."

Accordingly, it is desirable to provide orthopedic appliances that provide for controlled load sharing while providing the support necessary to prevent damage to a bone graft and/or other anatomical structure to allow for healing. Furthermore, it is desirable to provide orthopedic appliances that provide compressive forces between the attached bone structures to enhance ossification and healing of the corresponding bones.

SUMMARY

Embodiments disclosed herein solve the above-mentioned problems by providing a system and device for orthopedic implantation allowing for active compression between two or more osseous structures.

In some aspects, the techniques described herein relate to a compression plate configured to provide an active compression of two or more osseous structures, the compression plate including: a plug plate segment including a spring retaining member extending therefrom; a socket plate segment moveably coupled to the plug plate segment and receiving the spring retaining member therein; a plurality of bone screws configured to secure the compression plate to the two or more osseous structures, wherein each of the plug plate segment and the socket plate segment include at least one bone screw of the plurality of bone screws; and a spring disposed at the spring retaining member, wherein the spring is arranged to bias the socket plate segment towards the plug plate segment and thereby provide the active compression between the two or more osseous structures.

In some aspects, the techniques described herein relate to a spinal compression plate configured to transition between an open configuration and a closed configuration, the spinal compression plate including: a plurality of plate segments including at least a first plate segment and a second plate segment; a spring retaining member extending from the first plate segment and defining a spring channel therein; a spring retaining member recess defined by the second plate segment and receiving the spring retaining member therein, a spring biasing pin disposed at the second plate segment and extending through the spring channel, the spring biasing pin movably coupling the second plate segment to the first plate segment; and a spring disposed within the spring channel and engaging the spring biasing pin, wherein the spring biases the spring biasing pin and the second plate segment towards the first plate segment, thereby biasing the spinal compression plate towards the closed configuration.

In some aspects, the techniques described herein relate to a spinal compression plate configured to provide active compression between two or more vertebrae, including: an intermediate segment including a first spring retaining member and a second spring retaining member extending therefrom; a first plate segment receiving the first spring retaining member therein, wherein the first plate segment is translatable about the first spring retaining member; a second plate segment receiving the second spring retaining member therein, wherein the second plate segment is translatable about the second spring retaining member; a first spring housed within the first spring retaining member; and a second spring housed within the second spring retaining member, wherein the first spring biases the first plate segment towards the intermediate segment, wherein the second spring biases the second plate segment towards the intermediate segment.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current present disclosure will be apparent from the following detailed description of the embodiments and the accompanying drawing figures.

BRIEF DESCRIPTION OF THE DRAWINGS

Embodiments of the present disclosure are described in detail below with reference to the attached drawing figures, wherein.

Figure 1A:
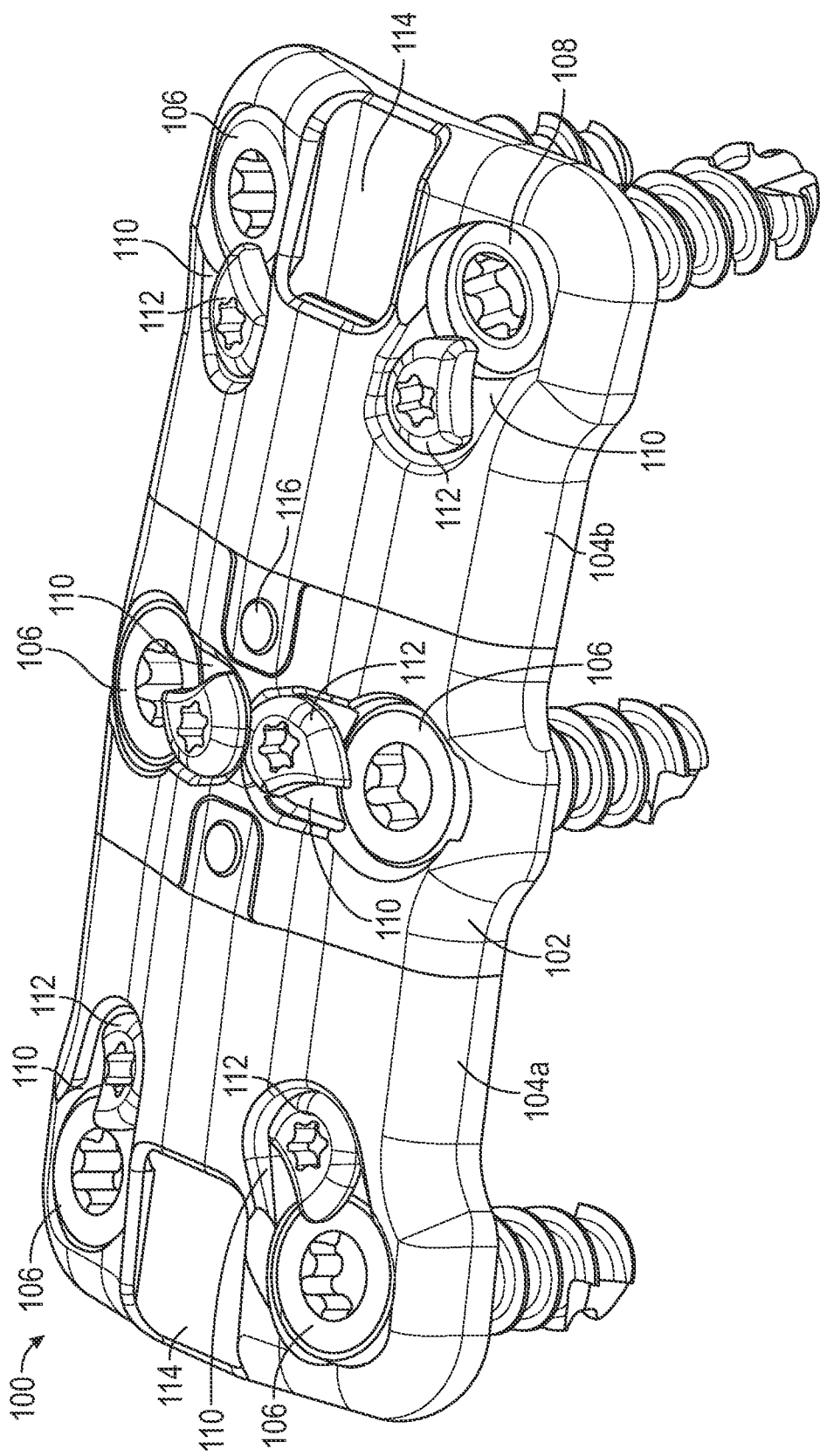
FIG. 1A depicts an exemplary perspective view of some embodiments of a compression plate.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The subject matter of embodiments of the invention is described in detail below to meet statutory requirements; however, the description itself is not intended to limit the scope of claims. Rather, the claimed subject matter might be embodied in other ways to include different steps or combinations of steps similar to the ones described in this document in conjunction with other present or future technologies. Minor variations from the description below will be obvious to one skilled in the art and are intended to be captured within the scope of the claimed invention. Terms should not be interpreted as implying any particular ordering of various steps described unless the order of individual steps is explicitly described.

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized, and changes can be made without departing from the scope of the invention. Therefore, the following detailed description is not to be taken in a limiting sense. The scope of embodiments of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Figure 1B:
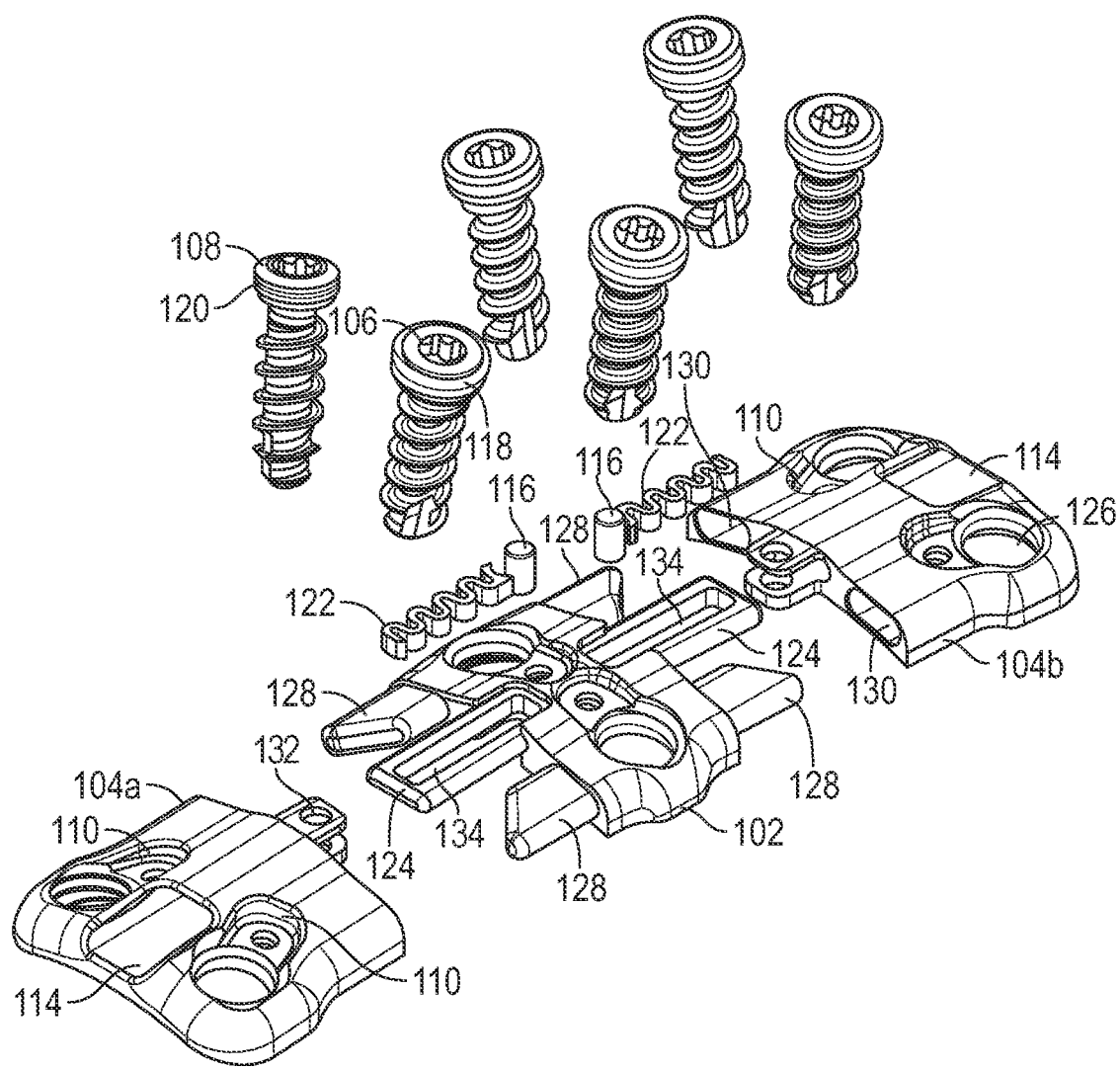
FIG. 1B depicts an exemplary exploded view of some embodiments of a compression plate.

Turning now to FIGS. 1A-1B, some embodiments of compression plate 100 are depicted. FIG. 1A illustrates some embodiments of compression plate 100 assembled. FIG. 1B illustrates and exploded view of some embodiments of compression plate 100. It is noted that some components, for example one or more locking screw heads 112 are removed from FIG. 1B for clarity purposes. One or more components of the depicted compression plates may be formed of any suitable material or combination of materials, including, but not limited to, titanium, aluminum, vanadium, Ti-6Al-4V (e.g., Ti64), and similar metals and alloys.

In some embodiments, compression plate 100 is curved to fit or conform with the curve of the surface it is to be attached to. For example, compression plate 100 may be curved about the vertical axis to conform with the curve of vertebrae. Additionally or alternatively, compression plate 100 may be curved about the horizontal axis to conform with the curve of the spine. In some embodiments, compression plate 100 is substantially flat.

In some embodiments, compression plate 100 may include any number of segments to attach or otherwise fasten to any number of vertebrae. For example, in some embodiments compression plate 100 includes a first plate segment 104a and a second plate segment 104b movably coupled to an intermediate plate segment 102. In such embodiments, intermediate plate segment 102 may be between first plate segment 104a and second plate segment 104b. For clarity purposes, embodiments disclosed herein reference the configuration illustrated in FIGS. 1A-1B, whereby compression plate 100 comprises three plate segments (e.g., intermediate plate segment 102, first plate segment 104a, and second plate segment 104b). However, some embodiments include more or less segments. For example, some embodiments of compression plate 100 may include two, four, five, six, or more segments. In some embodiments, compression plate 100 may comprise no intermediate plates. In some embodiments, compression plate 100 may comprise two or more intermediate plates.

In some embodiments, second plate segment 104b includes the same components as first plate segment 104a. In some embodiments, second plate segment 104b includes different components than first plate segment 104a. For purposes of clarity, embodiments of first plate segment 104a and second plate segment 104b are disclosed having substantially similar components and/or structures; thus, identical reference numerals are used. However, such a description is not intended to be limiting, as first plate segment 104a and second plate segment 104b may comprise differing components and/or structures depending on the arrangement of compression plate 100. Similarly, for purposes of clarity, intermediate plate segment 102 is discussed as having some components (e.g., spring retaining member 124) that are not depicted at first plate segment 104a or second plate segment 104b. However, components depicted at intermediate plate segment 102 may be additionally or alternatively disposed at first plate segment 104a and/or second plate segment 104b. Furthermore, components depicted at first plate segment 104a and/or second plate segment 104b may be additionally or alternatively disposed at intermediate plate segment 102.

In some embodiments and descriptions herein, a plate segment (e.g., intermediate plate segment 102) including spring retaining member 124 extending therefrom may be referred to as a plug plate segment. Further, in some embodiments and descriptions herein, a plate segment (e.g., first plate segment 104a) including spring retaining member recess 114 may be referred to as a socket plate segment. In some embodiments, and as discussed in greater detail below, compression plate 100 may comprise two plate segments. In such embodiments, compression plate 100 may comprise a plug plate segment and a socket plate segment. As will be discussed in greater detail below, spring retaining member recess 114 of the socket plate segment may receive spring retaining member 124 of the plug plate segment therein. Accordingly, the plug plate segment and socket plate segment may interact according to disclosed embodiments herein whereby spring 122 biases the plug plate segment and socket plate segment towards a closed configuration (i.e., towards one another).

In some embodiments, intermediate plate segment 102 includes one or more connectors 128. In some embodiments, first plate segment 104a and/or second plate segment 104b may include one or more connector recesses 130 for receiving the one or more connectors 128. The one or more connectors 128 may be structurally compatible with the one or more connector recesses 130 of first plate segment 104*a* and/or second plate segment 104*b* such that the one or more connectors 128 may slot within the one or more connector recesses 130.

Figure 3A:
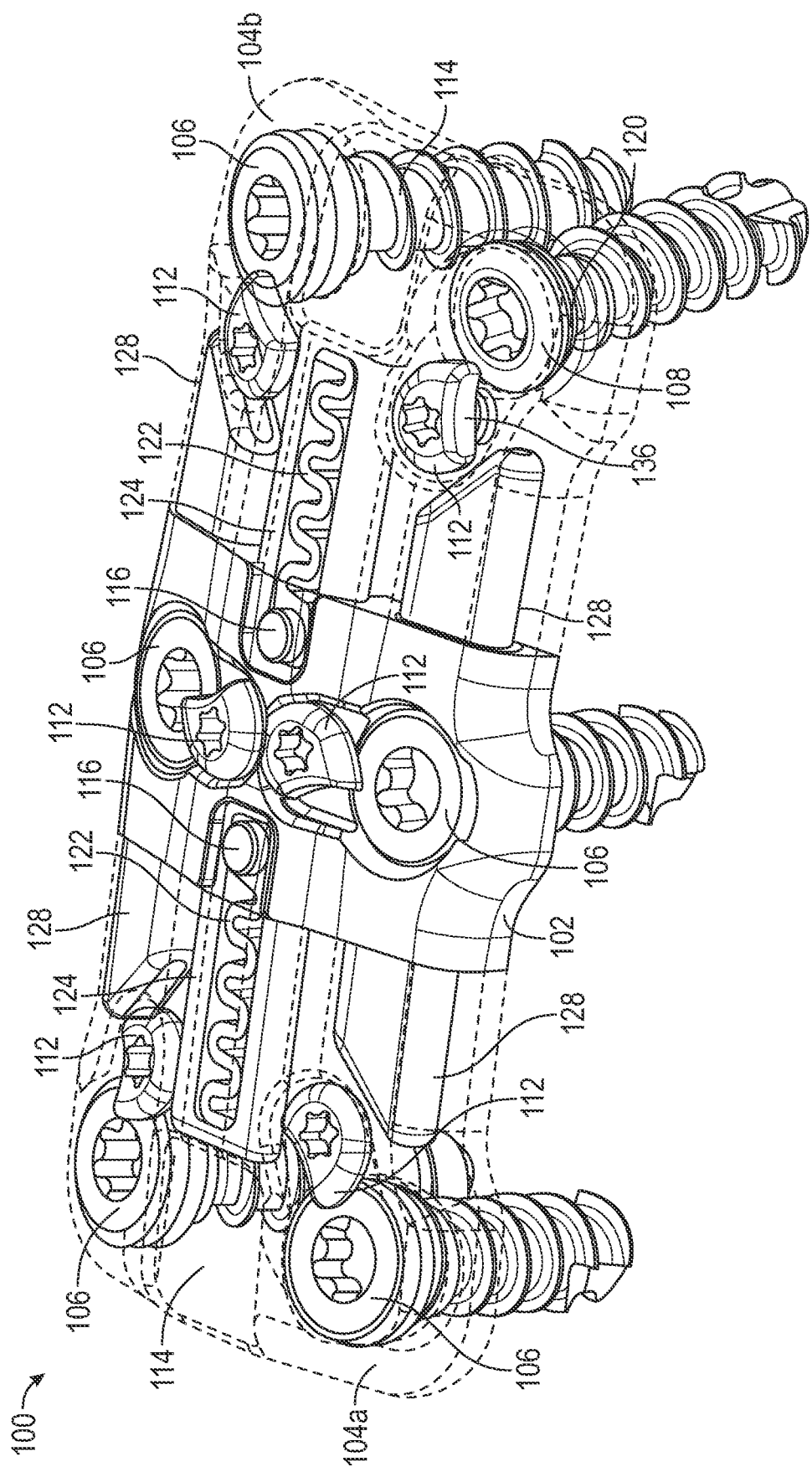
FIG. 3A depicts an exemplary perspective view of some embodiments of a compression plate in a closed configuration.
Figure 3B:
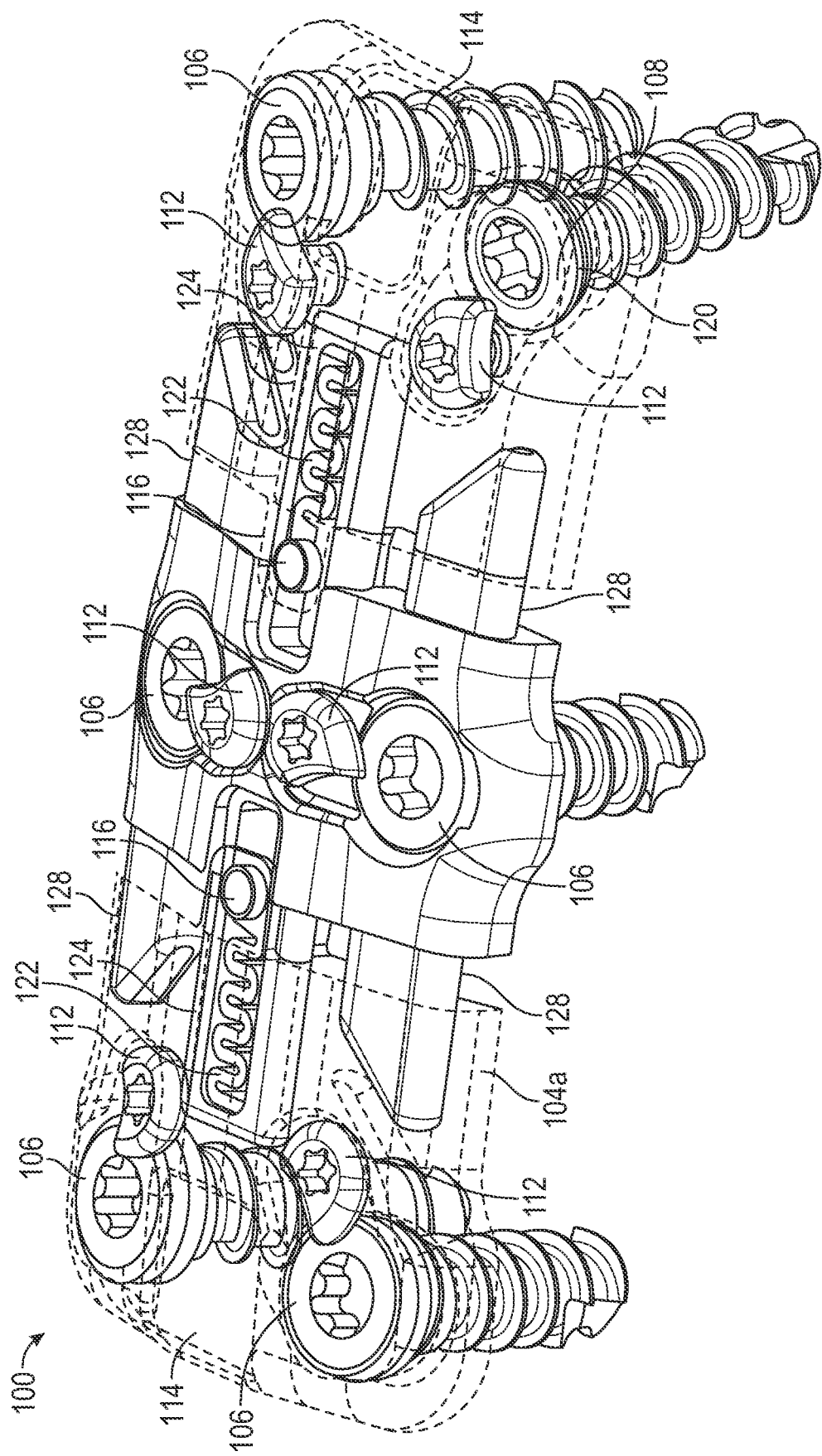
FIG. 3B depicts an exemplary perspective view of some embodiments of a compression plate in an open configuration.

In some embodiments, the one or more connectors 128 are partially or fully insertable into the one or more connector recesses 130. For example, as depicted in FIG. 3A, one or more connectors 128 may be inserted into one or more connector recesses 130 such that intermediate plate segment 102 abuts first plate segment 104*a* at the sides on which one or more connectors 128 and one or more connector recesses 130 are disposed, respectively. In some embodiments, the side of intermediate plate segment 102 may be flush against the side of first plate segment 104*a* such that no gap exists between intermediate plate segment 102 and first plate segment 104*a* (e.g., in the closed configuration illustrated in FIG. 3A). In some embodiments, one or more connectors 128 are partially insertable into one or more connector recesses 130. For example, as depicted in FIG. 3B, the one or more connectors 128 of intermediate plate segment 102 may not be fully inserted within the one or more connector recesses 130 of first plate segment 104*a*. Such a configuration may form a gap between intermediate plate segment 102 and first plate segment 104*a* (e.g., in the open configuration illustrated in FIG. 3B). The aforementioned description in regard to intermediate plate segment 102 and first plate segment 104*a* may be similarly applied to intermediate plate segment 102 and second plate segment 104*b*.

Figure 4:
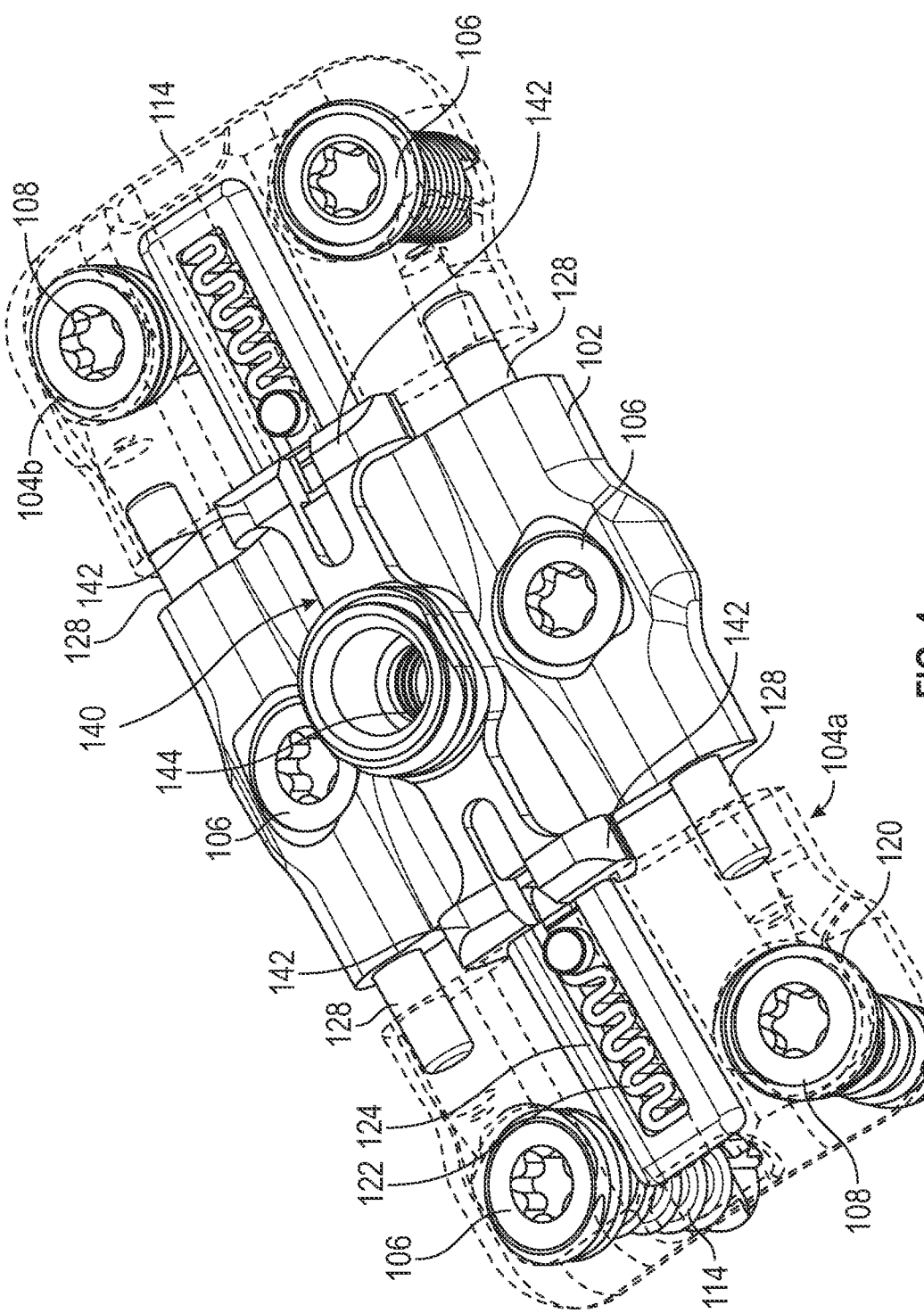
FIG. 4 depicts an exemplary perspective view of some embodiments of a compression plate having a retaining clip and in an open configuration.

The one or more connectors 128 may be any shape now known or later developed, including square, rectangular, round, and the like. In some embodiments, as depicted in FIG. 1B, the one or more connectors 128 are a trapezoidal shape. In some embodiments, as depicted in FIG. 4, the one or connectors 128 are cylindrically shaped. The connection between one or more connectors 128 and one or more connector recesses 130 may provide structural stability to compression plate 100 between the plurality of plate segments (e.g., between first plate segment 104*a* and intermediate plate segment 102).

Generally, compression plate 100 is configured to fasten or secure to a surface, such as osseous tissue. Compression plate 100 may be secured to the surface using one or more fasteners. For example, some exemplary fasteners include, but are not limited to, pedicle screws, nails, rods, bolts, and any other fasteners.

In some embodiments, turning back to FIGS. 1A and 1B, compression plate 100 includes fasteners in the form of one or more bone screws 106. In such embodiments, one or more bone screws 106 may be attached to any one or more of intermediate plate segment 102, first plate segment 104*a*, and second plate segment 104*b*. In some embodiments, the one or more bone screws 106 are threaded bone screws. For example, the one or more bone screws 106 are rotatably driven or otherwise secured within one or more apertures 126 on compression plate 100. As will be discussed below, in some embodiments the one or more apertures 126 may be threaded allowing for rotational attachment and locking of one or more bone screws 106 (e.g., locking bone screw 108) within the one or more apertures 126.

In some embodiments, the heads of the one or more bone screws 106 are counter-sunk style. For example, the heads of the one or more bone screws 106 may be flat, oval, or bulge styles. In other embodiments, the heads of the one or more bone screws 106 are non-countersunk style. For example, the heads of the one or more bone screws 106 may be binding, button, cheese, fillister, flange, hex, pan, round, socket, low socket, square, or truss styles. Generally, the one or more bone screws 106 may have any driving recess or combination of driving recesses now known or later developed, including slotted, Phillips, hex, hex socket, square, Torx®, spanner, and any similar driving recess.

In some embodiments, the one or more bone screws 106 may be formed from any suitable material for orthopedic applications, such as for use as a spinal implant. In some embodiments, the one or more bone screws 106 may be formed from any suitable material now known or later developed, including, but not limited to, titanium, titanium alloy, stainless steel, Cobalt-Chromium Alloy, Polyetheretherketone, and the like.

Generally, one or more bone screws 106 may be located at various locations of compression plate 100 to provide a desired balance between stability and flexibility. In some embodiments, the one or more bone screws 106 are located at the corners of compression plate 100. For example, the one or more bone screws 106 may be located near the outer side of first plate segment 104*a* (i.e., the side furthest from intermediate plate segment 102) and the outer side of second plate segment 104*b* (i.e., the side furthest from intermediate plate segment 102). In some embodiments, the one or more bone screws 106 may be located near the center of intermediate plate segment 102.

Compression plate 100 includes various locking components that prevent compression plate 100 from becoming unfastened from the surface to which it is attached. In some embodiments, compression plate 100 includes locking bone screw 108. Generally, locking bone screw 108 enhances the security of compression plate 100 by preventing compression plate 100 from becoming detached from the surface to which it is attached. Locking bone screw 108 does so by being resistant to "backing out"-a common problem of screws in a dynamic environment (such as that of a human spine or other osseous tissue). In some embodiments, locking bone screw 108 may be coupled to intermediate plate segment 102, first plate segment 104*a*, second plate segment 104*b*, or any combination thereof. In some embodiments, compression plate 100 includes a singular locking bone screw 108. In some embodiments, as depicted in FIG. 4 (discussed below), compression plate 100 includes more than one locking bone screw 108. In some embodiments, compression plate 100 includes no locking bone screws.

There are various means by which locking bone screw 108 may be prevented from backing out of the corresponding aperture 126 on compression plate 100. In some embodiments, the threaded locking bone screw head 120 of locking bone screw 108 prevents locking bone screw 108 from backing out. For example, threaded locking bone screw head 120 may have a different thread pattern from that of threading located internally on the corresponding aperture 126 of compression plate 100. In exemplary embodiments, threading of threaded locking bone screw head 120 may be in a first direction and threading inside aperture 126 may be in a second direction, the first direction and second direction being opposite directions. By providing a mismatch in thread patterns between threaded locking bone screw head 120 and the corresponding aperture 126, locking bone screw 108 may be unable to unscrew or backout from aperture 126. In such a configuration, as locking bone screw 108 is rotationally driven into the surface (e.g., vertebrae), threaded locking bone screw head 120 enters into aperture 126. With opposing thread patterns between threaded locking bone screw head 120 and aperture 126, as threaded locking bone screw head 120 is rotated within aperture 126, the threads create torsional friction such that once locking bone screw 108 is fully driven, threaded locking bone screw head 120 is bound within aperture 126 thereby preventing rotation in the opposite direction.

In some embodiments, the threading on the shank of locking bone screw 108 may be a different thread pattern from that of the corresponding aperture 126 on compression plate 100. The mismatched threads on the shank of locking bone screw 108 and the corresponding aperture 126 may form a friction fit. The threading on the shank of the locking bone screw 108 may be formed through SPIRALOCK thread forming to create a friction fit between the bone screw 108 and corresponding aperture 126. In such embodiments, the mismatched threading between the shank of locking bone screw 108 and the threading of aperture 126 would function in a substantially similar manner to the mismatch between threaded locking bone screw head 120 and aperture 126, as described above. Similarly, locking bone screw 108 would be prevented from backing out of aperture 126 once rotationally driven into aperture 126. In some embodiments, locking bone screw 108 and aperture 126 on compression plate 100 are cold-welded together. For example, locking bone screw 108 and aperture 126 may include mismatched threading such that they become frictionally locked together when locking bone screw 108 is driven into aperture 126.

As discussed above with regard to the one or more bone screws 106, locking bone screw 108 may be formed from any suitable material now known or later developed, including, but not limited to titanium and titanium alloy. Further, locking bone screw 108 may have any suitable head style and driving recess now known or later developed.

In some embodiments, locking bone screw 108 and the corresponding aperture 126 are located on intermediate plate segment 102, first plate segment 104a, and/or second plate segment 104b. As discussed above with regard to the one or more bone screws 106, locking bone screw 108 and the corresponding aperture 126 may be located on the outer end of first plate segment 104a and/or second plate segment 104b. In other embodiments, locking bone screw 108 may be located on intermediate plate segment 102, such as to replace one or more bone screws 106 depicted in FIG. 1A.

Figure 2A:
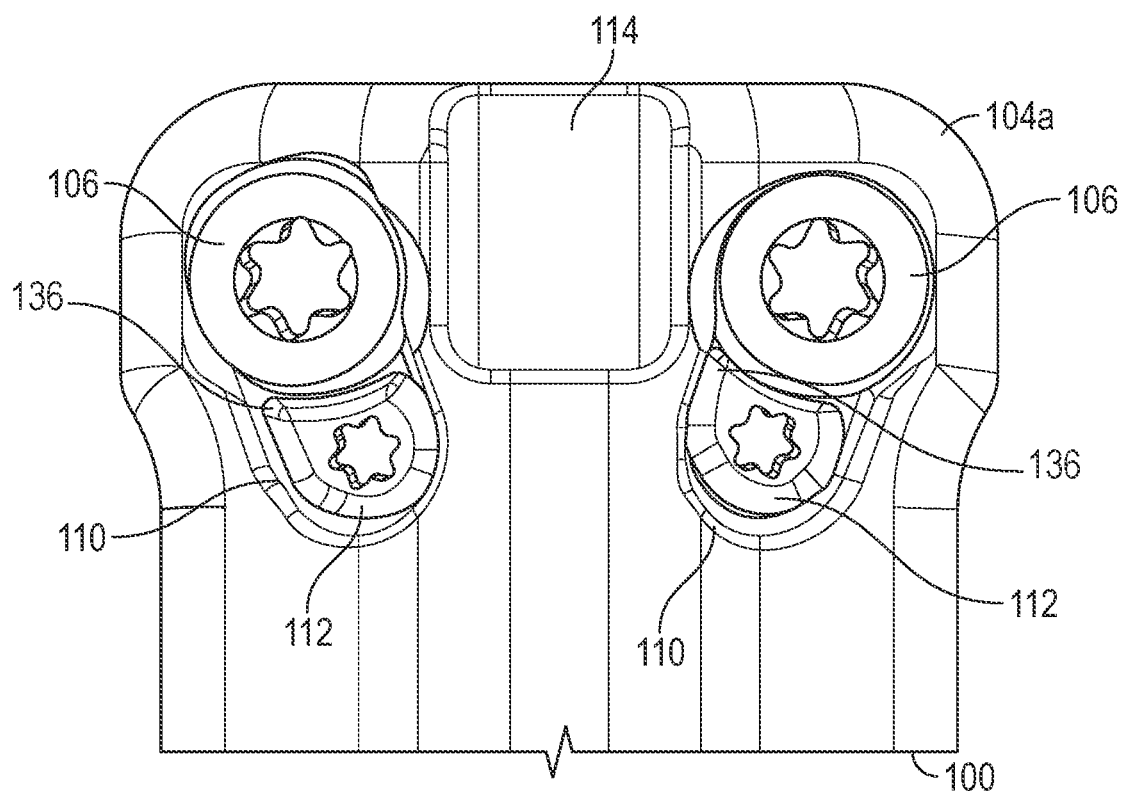
FIG. 2A depicts an exemplary top view of some embodiments of a compression plate with screws in an unlocked configuration.
Figure 2B:
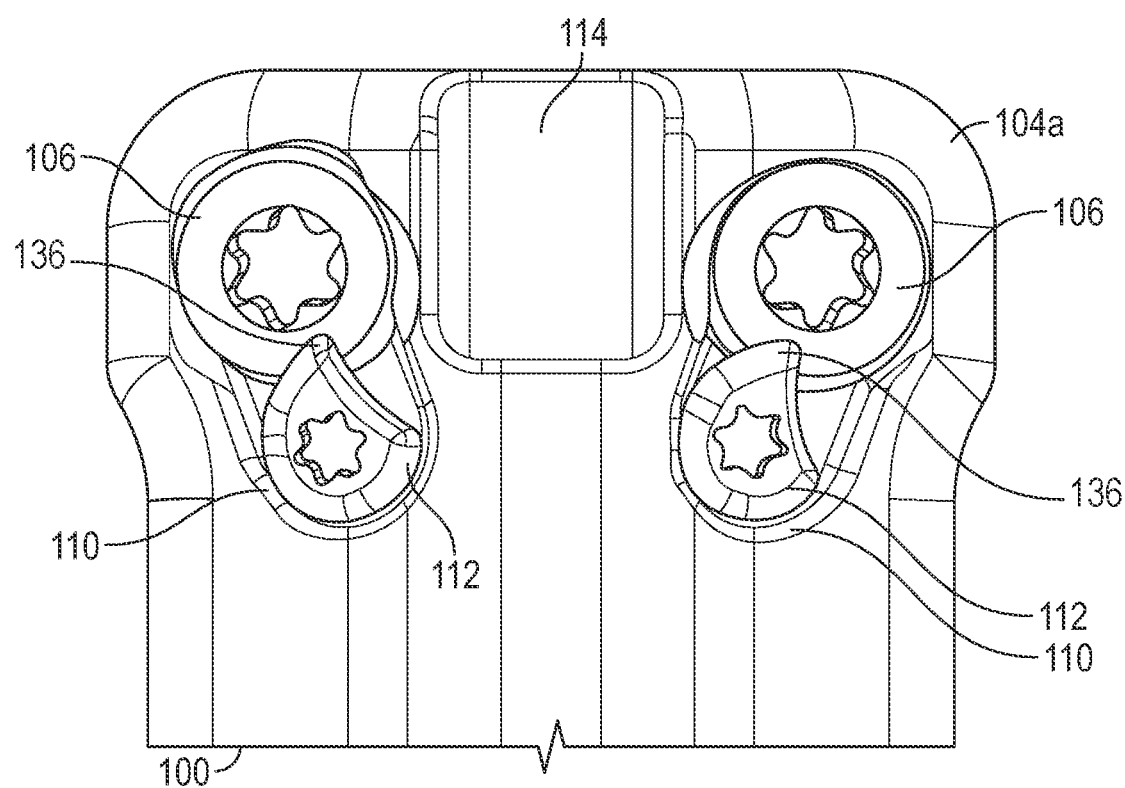
FIG. 2B depicts an exemplary top view of some embodiments of a compression plate with screws in a locked configuration.

Turning now to FIGS. 2A-2B, one or more locking screw heads 112 are depicted. In some embodiments, compression plate 100 includes an additional or alternative mechanism for preventing compression plate 100 from becoming unfastened from the surface to which it is secured. For example, in some embodiments compression plate 100 includes one or more locking screw heads 112. As discussed above with regard to the one or more bone screws 106, the one or more locking screw heads 112 may be formed from any suitable material now known or later developed, including, but not limited to, titanium and titanium alloy. Further, the one or more locking screw heads 112 may have any suitable head style and driving recess now known or later developed.

In some embodiments, the one or more locking screw heads 112 are situated within one or more screw head recesses 110. In some embodiments, the one or more locking screw heads 112 and the one or more screw head recesses 110 are located at the top surface of compression plate 100 and adjacent the one or more apertures 126 and one or more bone screws 106.

In some embodiments, the one or more locking screw heads 112 prevent the one or more bone screws 106 from backing out of the aperture 126 by covering the one or more bone screws 106. Thus, if the one or more bone screws 106 experience an outward force with respect to the secured surface, the one or more locking screw heads 112 may secure the one or more bone screws 106 within aperture 126 and prevent the one or more bone screws 106 from exiting therethrough.

FIG. 2A depicts one or more locking screw heads 112 in an unlocked configuration. Each of the one or more locking screw heads 112 may include a protrusion 136 that extends outwardly towards aperture 126. As will be discussed below, the shape of one or more locking screw heads 112 and protrusions 136 is such that when rotated, protrusion 136 covers aperture 126. When in an unlocked configuration, protrusions 136 of the one or more locking screw heads 112 do not overlap the heads of the one or more bone screws 106. Thus, the one or more bone screws 106 can be unscrewed and removed from aperture 126 and/or the surface without the interference of the one or more locking screw heads 112.

FIG. 2B depicts one or more locking screw heads 112 in a locked position. In the locked position, the protrusions 136 of the one or more locking screw heads 112 overlap the heads of the one or more bone screws 106. Thus, the one or more locking screw heads 112 will interfere and prevent the one or more bone screws 106 from being unscrewed or removed from the apertures in which they are located. In some embodiments, one or more locking screw heads 112 may be secured in the locked position once rotated thereto.

While not depicted herein, additional backout prevention mechanisms may be incorporated or otherwise used with compression plate 100 without departing from the scope of the disclosure. For example, in some embodiments compression plate 100 includes a slidable member that covers, partially or fully, aperture 126 and the one or more bone screws 106 once driven into the surface. In a manner similar to one or more locking screw heads 112, the slidable member may prevent backout of one or more bone screws 106 from the surface. In some embodiments, the slidable member may be secured in the locked position once covering aperture 126 and the one or more bone screws 106.

The various backout prevention mechanisms disclosed herein may be used individually or in combination in embodiments of compression plate 100. For example, as shown in FIG. 1A, compression plate 100 may have both locking bone screw 108 and one or more locking screw heads 112. In some embodiments, such as shown in FIG. 4, compression plate 100 may have at least one locking bone screw 108 while not having locking screw heads 112. Thus, compression plate 100 may have any suitable combination or arrangement of backout prevention mechanisms described above for preventing compression plate 100 from becoming loosened or unfastened.

Turning back to FIG. 1B, compression plate 100 may include at least one spring 122 providing compressive forces to compression plate 100. For example, utilizing at least one spring 122 in compression plate 100 allows for compression plate 100 to provide active compression between the surfaces (e.g., between two or more vertebrae) to which compression plate 100 is attached. As discussed above, biasing (i.e., actively compressing) two or more osseous structures together enhances ossification of the tissue, thereby increasing strength and density of the osseous structures.

Spring 122 may be formed from any suitable material now known or later developed including metal, silicon, plastic, and the like. In some embodiments, spring 122 comprises a nickel-titanium alloy (e.g., nitinol). Nitinol may be particularly useful for the formation of spring 122, due to having superelastic properties. Such a property allows for spring 122 to undergo significant deformations (e.g., compression) while still reverting back to the original shape. Furthermore, since nitinol will retain the shape of spring 122 for a long period of time (e.g., years), spring 122 will maintain stable active compression between components of compression plate 100, and therefore the attached osseous structures, for the entire period of which compression plate 100 is implanted.

Spring 122 may be housed within spring channel 134 defined by spring retaining member 124. Spring channel 134 provides a cavity in which spring 122 may compress and expand along a single axis (e.g., along the vertical axis, as depicted in FIG. 7B). As illustrated in FIG. 1B, spring retaining member 124 extends outwardly from intermediate plate segment 102 and towards first plate segment 104a and second plate segment 104b. Again, as mentioned above, exemplary illustrations depict three segments of compression plate 100 (i.e., first plate segment 104a, intermediate plate segment 102, and second plate segment 104b). However, additional segments (e.g., an additional intermediate plate) and less segments (e.g., lacking intermediate plate segment 102 or second plate segment 104b) may be used with compression plate 100 without departing from the scope of the disclosure. In these embodiments, spring retaining member 124 may extend from whichever segment necessary to house spring 122 and provide active compression between the segments.

In some embodiments, an end of spring 122 is attached to or within spring channel 134 of spring retaining member 124. For example, an end of spring 122 may be coupled to a wall defining spring channel 134 using soldering, welding, adhesives, etc. In another example, an end of spring 122 may be coupled to spring channel 134 using a pin similar to spring biasing pin 116 discussed below. In some embodiments, based on the housing and structure of compression plate 100, spring 122 is maintained within spring channel 134 while not being attached to the inside of spring retaining member 124.

In some embodiments, spring retaining member 124 slots within spring retaining member recess 114 disposed at first plate segment 104a and/or second plate segment 104b. For example, spring retaining member 124 may slot within spring retaining member recess 114 such that the sides of intermediate plate segment 102 are flush or substantially flush against first plate segment 104a and/or second plate segment 104b. Similar to the description above regarding spring retaining member 124, in embodiments in which compression plate 100 has two, four, or more segments, spring retaining member recess 114 may be disposed on whichever segment necessary to receive spring retaining member 124 and house spring 122 to provide active compression between segments. For example, in some embodiments an additional intermediate plate (not depicted) may be included in compression plate 100. In such embodiments, the additional intermediate plate may include a spring retaining member recess disposed at one end to interface with spring retaining member 124 an intermediate plate segment 102. Further, the additional intermediate plate may include a spring retaining member disposed at the end opposite the spring retaining member recess for interfacing with spring retaining member recess 114 of second plate segment 104b.

In some embodiments, spring retaining member 124 may provide structural support for the connection between segments of compression plate 100 (e.g., first plate segment 104a, second plate segment 104b, and intermediate plate segment 102). In such embodiments, spring retaining member 124, extending from intermediate plate segment 102, may be arranged to slot within a spring retaining member recess 114 located at an adjacent segment. Based on the shape of spring retaining member 124 and spring retaining member recess 114, slotting spring retaining member 124 within spring retaining member recess 114 (as shown in FIG. 3A) may provide structural stability to compression plate 100. For example, as depicted spring retaining member 124 and spring retaining member recess 114 comprise a rectangular shape. As such, when spring retaining member 124 is received within spring retaining member recess 114, torsional forces between intermediate plate segment 102 and first plate segment 104a are precluded.

In some embodiments, the shape of spring retaining member 124 and spring retaining member recess 114 may be adjusted based on the desired structural integrity of compression plate 100. For example, in some embodiments spring retaining member 124 and spring retaining member recess 114 may comprise a circular shape thereby allowing rotation between intermediate plate segment 102 and first plate segment 104a.

In some embodiments, a spring biasing pin 116 is coupled to spring 122 at one end. In some embodiments, the end of spring 122 attached to spring biasing pin 116 is opposite the end of spring 122 contacting or coupling the wall of spring channel 134. As will be discussed in greater detail below, contact and/or coupling of spring 122 at both ends (one end at a wall of spring channel 134 and one end at spring biasing pin 116) causes active compression of the two corresponding segments (e.g., first plate segment 104a against intermediate plate segment 102).

In some embodiments, spring biasing pin 116 is attached to a plate segment (e.g., first plate segment 104a) at pin retention aperture 132 extending from first plate segment 104a (as depicted in FIG. 1B). In some embodiments, both first plate segment 104a and second plate segment 104b include pin retention aperture 132 for receiving and coupling a spring biasing pin 116. Spring biasing pin 116 may be coupled to a corresponding pin retention aperture 132 using any technique now known or later developed, including, but not limited to, pinning, welding, and similar fastening techniques.

In reference to FIG. 1B, the process of coupling plate segments (e.g., coupling first plate segment 104a to intermediate plate segment 102) is briefly discussed. In some embodiments, spring 122 is placed within spring channel 134. In some embodiments, spring 122 is partially compressed prior to placement within spring channel 134. For example, the length of spring 122 is greater than the length of spring channel 134. In such embodiments, spring 122 may constantly bias compression plate 100 towards the closed configuration, as discussed below. In some embodiments, the length of spring 122 is roughly the same length as spring channel 134 and thus is not compressed prior to placement within spring channel 134.

In some embodiments, the intermediate plate segment 102 is translated towards first plate segment 104a. During translation, spring retaining member 124 is received within spring retaining member recess 114. In some embodiments, one or more connectors 128 extending from intermediate plate segment 102 are received within one or more connector recesses 130 of first plate segment 104a. Once spring retaining member 124 is fully received within spring retaining member recess 114, pin retention aperture 132 is arranged over the proximal end (i.e., the end closest to intermediate plate segment 102) of spring channel 134. In some embodiments, spring biasing pin 116 is inserted into and through pin retention aperture 132 such that spring biasing pin 116 extends through spring channel 134. Following insertion of spring biasing pin 116 through pin retention aperture 132 and spring channel 134, in some embodiments spring biasing pin 116 is coupled to pin retention aperture 132. In some embodiments, spring 122 is coupled to spring biasing pin 116. In some embodiments, such as that depicted in FIG. 1B, spring 122 may comprise a shape configured to conform to spring biasing pin 116.

Similar steps to those described above may be used to couple second plate segment 104b to intermediate plate segment 102. Connection of second plate segment 104b to intermediate plate segment 102 may occur prior to, in conjunction with, or following connection of first plate segment 104a to intermediate plate segment 102. Furthermore, as mentioned previously, less or more steps may be taken to connect less or more segments in embodiments in which compression plate 100 comprises less or more segments than depicted.

By coupling spring biasing pin 116 to pin retention aperture 132, spring 122 biases first plate segment 104a towards intermediate plate segment 102 by exerting force against spring biasing pin 116 at one end and spring channel 134 at the other end. For example, upon movement of first plate segment 104a away from intermediate plate segment 102, spring 122 is compressed. In some embodiments, spring 122 will bias or otherwise press against spring biasing pin 116 such that first plate segment 104a is pressed towards intermediate plate segment 102. Such movement between intermediate plate segment 102 and first plate segment 104a is discussed in greater detail below in relation to the open configuration (e.g., see FIG. 3B) and the closed configuration (e.g., see FIG. 3A) of compression plate 100.

FIG. 3A depicts compression plate 100 in a closed configuration. In some embodiments, while compression plate 100 is in a closed configuration, first plate segment 104a and second plate segment 104b abut the sides of intermediate plate segment 102. In such embodiments, the one or more connectors 128 of intermediate plate segment 102 are fully seated within the corresponding one or more connector recesses 130 of first plate segment 104a and second plate segment 104b.

Generally, when compression plate 100 is in a closed configuration, the displacement of spring 122 from its equilibrium position (i.e., length) with respect to the equation F=−kx where F is the force applied by a spring, k is the spring constant, and x is the spring displacement from its equilibrium position is smaller relative to the displacement of spring 122 from its equilibrium position when compression plate 100 is in an open position. In some embodiments, when compression plate 100 is in a closed configuration, spring 122 is approximately in its equilibrium position. Thus, when spring 122 is approximately in its equilibrium position, it provides little or no force to intermediate plate segment 102 and first plate segment 104a or second plate segment 104b. In other embodiments, when compression plate 100 is in a closed configuration, the displacement of spring 122 from its equilibrium position is nonzero, providing some force to compress first plate segment 104a and/or second plate segment 104b towards intermediate plate segment 102.

FIG. 3B depicts compression plate 100 in an open configuration. When in an open configuration, first plate segment 104a and second plate segment 104b do not contact the sides of intermediate plate segment 102. In some embodiments, the one or more connectors 128 of intermediate plate segment 102 are partially seated within the corresponding one or more connector recesses 130 of first plate segment 104a and second plate segment 104b.

Broadly, when compression plate 100 is in an open configuration, spring 122 may be compressed relative to the length of spring 122 when compression plate 100 is in a closed configuration. More specifically, spring 122 may be displaced farther from its equilibrium position while compression plate 100 is in an open position relative to the displacement of spring 122 while compression plate 100 is in a closed position. Thus, the force exerted by spring 122 may be greater while compression plate 100 is in an open position than when compression plate 100 is in a closed position.

Said another way, as the distance between intermediate plate segment 102 and first plate segment 104a or second plate segment 104b increases, the force exerted by spring 122 increases. The force exerted by spring 122 may bias first plate segment 104a and second plate segment 104b towards intermediate plate segment 102 (e.g., closer to the equilibrium position of spring 122). Thus, spring 122 may always provide a force such that first plate segment 104a and second plate segment 104b are biased towards intermediate plate segment 102 when compression plate 100 is attached to a dynamic surface. This may prove advantageous, as spring 122 may allow compression plate 100 to provide active compression to the dynamic surface to which it is attached.

In some embodiments, spring 122 may be configured to provide lesser or greater compressive forces to compression plate 100. For example, one or both of the equilibrium length and/or the spring force of spring 122 may be altered to adjust the compressive forces based on the application of compression plate 100. In some embodiments, spring 122 may be configured to more easily compress and thereby allow compression plate 100 to transition to the open configuration with a lower amount of force. In some embodiments, spring 122 may be configured to more heavily resist compression and thereby preclude compression plate 100 from transitioning to the open configuration. Differences in spring 122 and thus the corresponding compressive forces may be determined based on the application of compression plate 100. Additionally, in some embodiments in which two or more springs 122 are used, the two or more springs 122 may comprise differences in compressive forces. For example, in the case of vertebrae, it may be advantageous to allow two vertebrae to separate by decreasing the compressive forces of the intervening spring 122 (e.g., spring 122 between second plate segment 104b and intermediate plate segment 102). Similarly, it may be advantageous to prevent two vertebrae from separating by increasing the compressive forces of the intervening spring 122 (e.g., spring 122 between first plate segment 104a and intermediate plate segment 102). As such, compression plate 100 is heavily adaptable depending on the downstream application.

Turning now to FIG. 4, some embodiments of compression plate 100 are depicted. In some embodiments, a retaining clip 140 may be attached to compression plate 100. Retaining clip 140 may hold compression plate 100 in an open configuration, as illustrated in FIG. 4. Further, retaining clip 140 may be utilized in insertion and attachment of compression plate 100 to a surface. For example, retaining clip 140 may hold compression plate 100 in an open configuration while one or more bone screws 106 are screwed into the adjacent surface (e.g., vertebrae). Furthermore, in some embodiments retaining clip 140 may maintain space between intermediate plate segment 102 and various plate segments (e.g., first plate segment 104a and/or second plate segment 104b) such that spinal graft material may be injected into the intervening space. Such capabilities of injecting bone graft material may be advantageous in applications of compression plate 100 whereby the attached osseous structures are damaged between one another. For example, in some embodiments compression plate 100 may be used in conjunction with one or more interbody cages. In such embodiments, injection of bone graft material at the site of the interbody cage (e.g., between two vertebrae) may substantially aid in the healing of the area.

Figure 6:
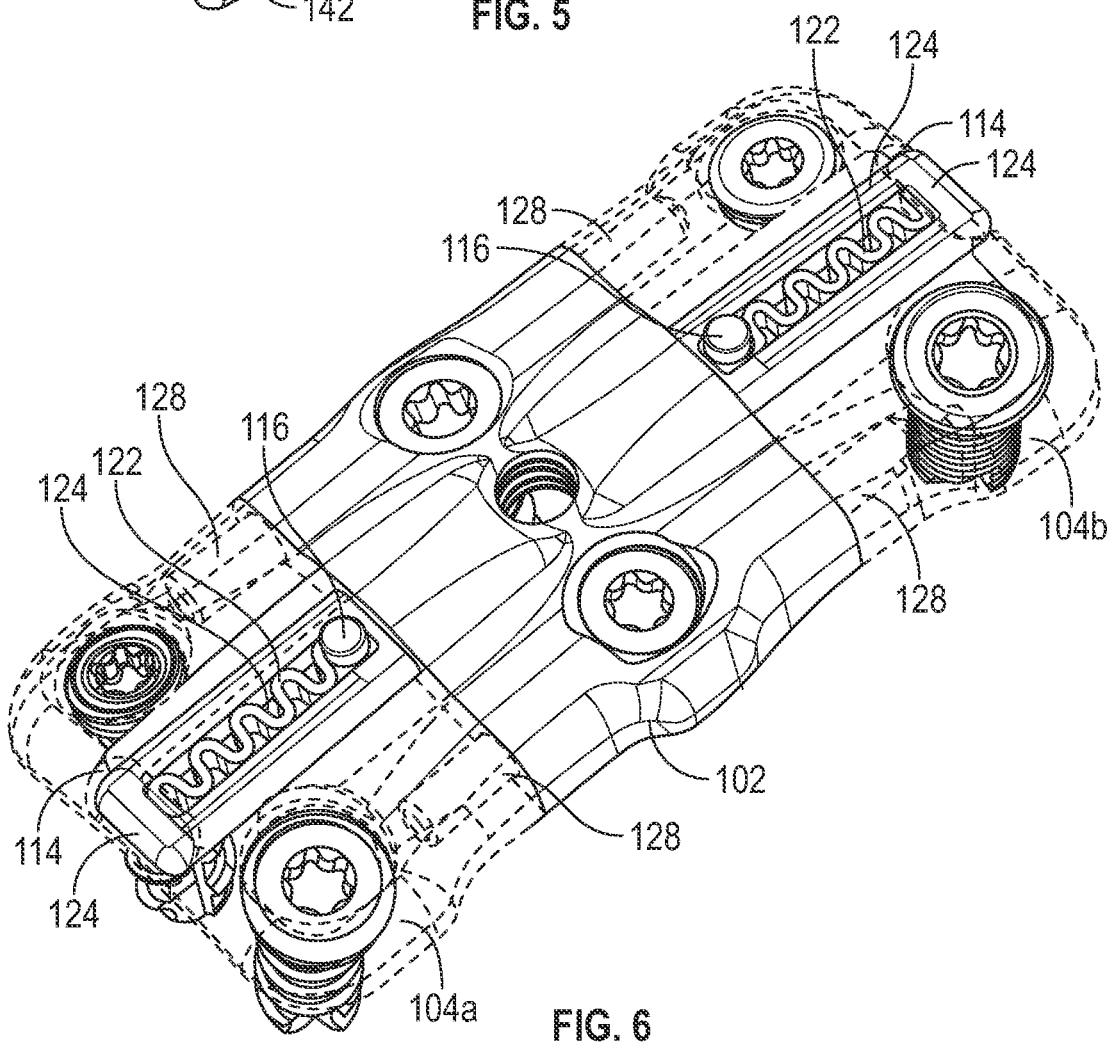
FIG. 6 depicts an exemplary perspective view of some embodiments of a compression plate in a closed configuration.

In addition to providing a space for injection of material, such as bone graft material, maintaining compression plate 100 in an open configuration during insertion and attachment may provide additional benefits, in some scenarios. For example, by attaching compression plate 100 to osseous structures (e.g., two or more vertebrae) while in the open configuration, upon removal of retaining clip 140, compression plate 100 immediately provides compressive forces to the attached osseous structures by transitioning towards the closed configuration, such as depicted in FIG. 6. Such a procedure may aid in, for example, retention of an interbody cage between two or more vertebrae. It is noted, however, retaining clip 140 may be removed from compression plate 100 at times other than following attachment of compression plate 100 to the osseous structures.

Figure 5:
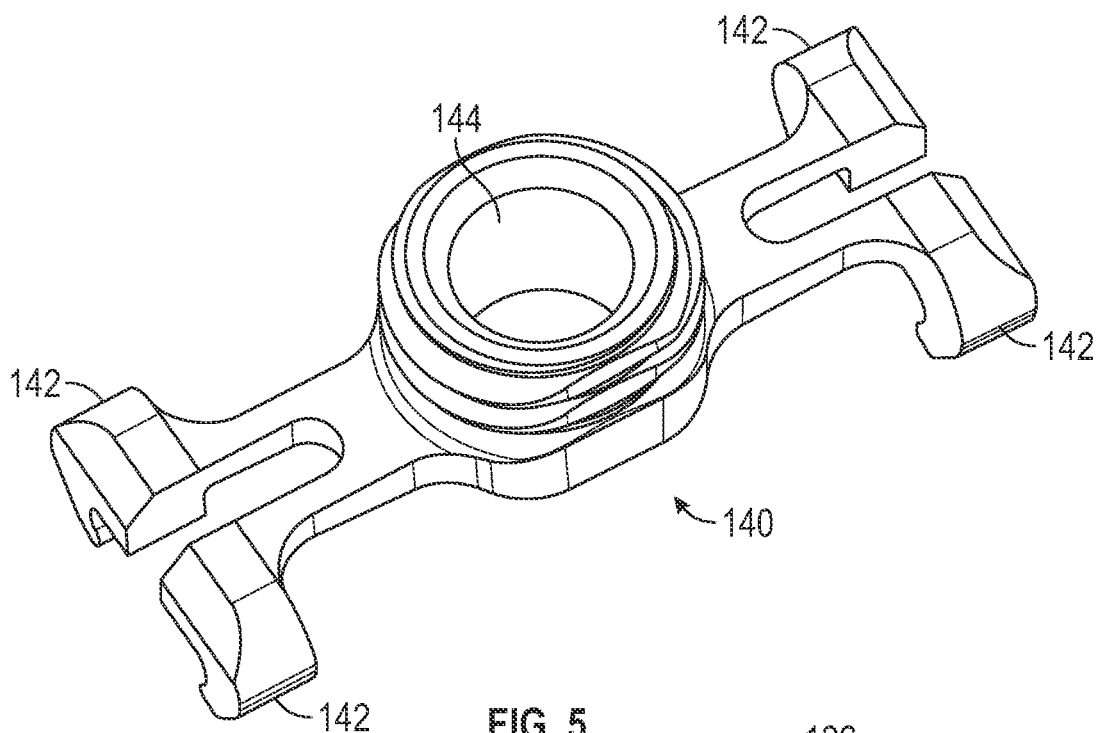
FIG. 5 depicts an exemplary perspective view of some embodiments of a retaining clip.

As illustrated in FIG. 5, retaining clip 140 may include one or more clip arms 142 and a clip aperture 144. In some embodiments, the one or more clip arms 142 may be configured to attach (e.g., snap, click, etc.) to spring retaining member 124, as illustrated in FIG. 4. In some embodiments, the one or more clip arms 142 do not attach to components of compression plate 100.

In some embodiments, the one or more clip arms 142 are configured to maintain space between intermediate plate segment 102 and first plate segment 104a and/or second plate segment 104b. In such embodiments, the width of the one or more clip arms 142 is predetermined to maintain a desired compression and equilibrium displacement for spring 122. Thus, when one or more bone screws 106 are used to attach compression plate 100 to a surface, retaining clip 140 may then be removed and the desired equilibrium displacement and compression of spring 122 achieved.

In some embodiments, clip aperture 144 may be configured to receive a fastener. In such embodiments, clip aperture 144 may receive a fastener to provide stability to compression plate 100 during insertion and attachment to a surface. For example, intermediate plate segment 102 may be stabilized by attaching a fastener to the surface below through clip aperture 144 and an aperture in intermediate plate segment 102. The fastener may then be removed after intermediate plate segment 102 and compression plate 100 as a whole are stabilized with one or more bone screws 106.

Figure 8A:
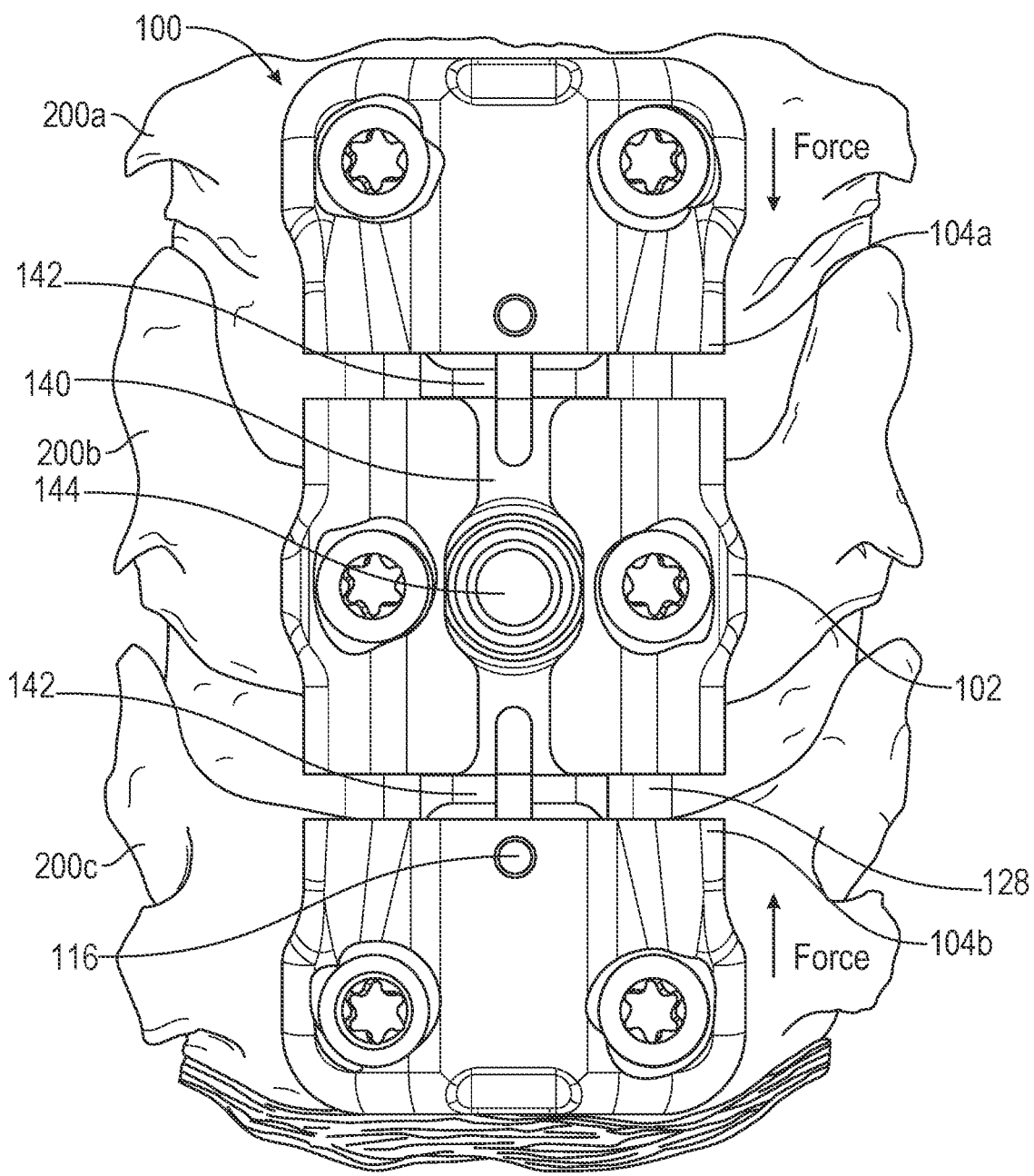
FIG. 8A depicts an exemplary top view of some embodiments of a compression plate with a retaining clip following attachment to a vertebral segment.

In some embodiments, retaining clip 140 may be formed from any suitable material now known or later developed, including, but not limited to, polymer, titanium, titanium alloy, and the like. In some embodiments, retaining clip 140 is formed from a bioresorbable material, such as a bioresorbable polymer. In such embodiments, as depicted in FIG. 8A, retaining clip 140 may be left inserted to resorb, allowing active compression by compression plate 100 to begin.

Figure 7A:
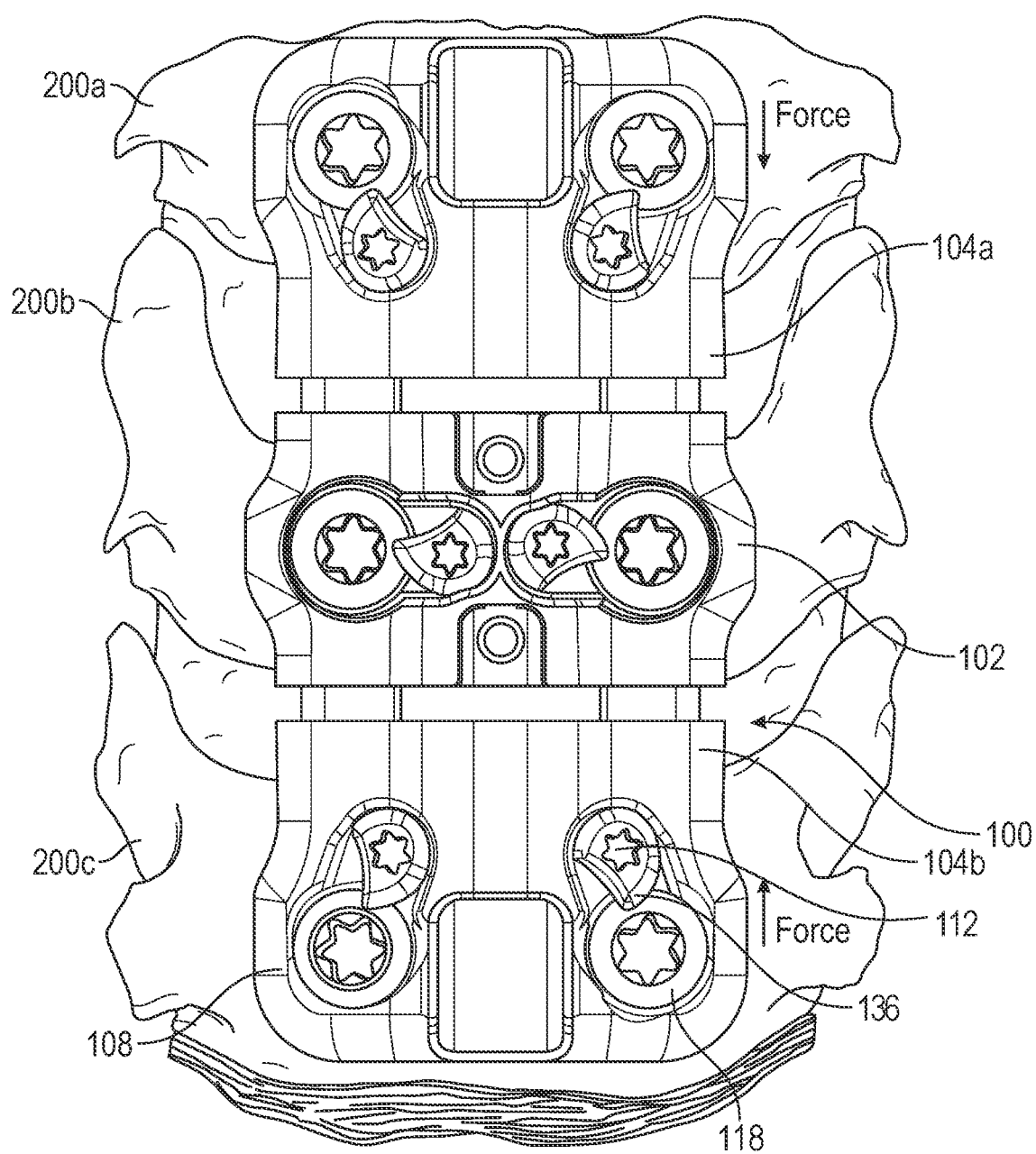
FIG. 7A depicts an exemplary top view of some embodiments of a compression plate following attachment to a vertebral segment.
Figure 7B:
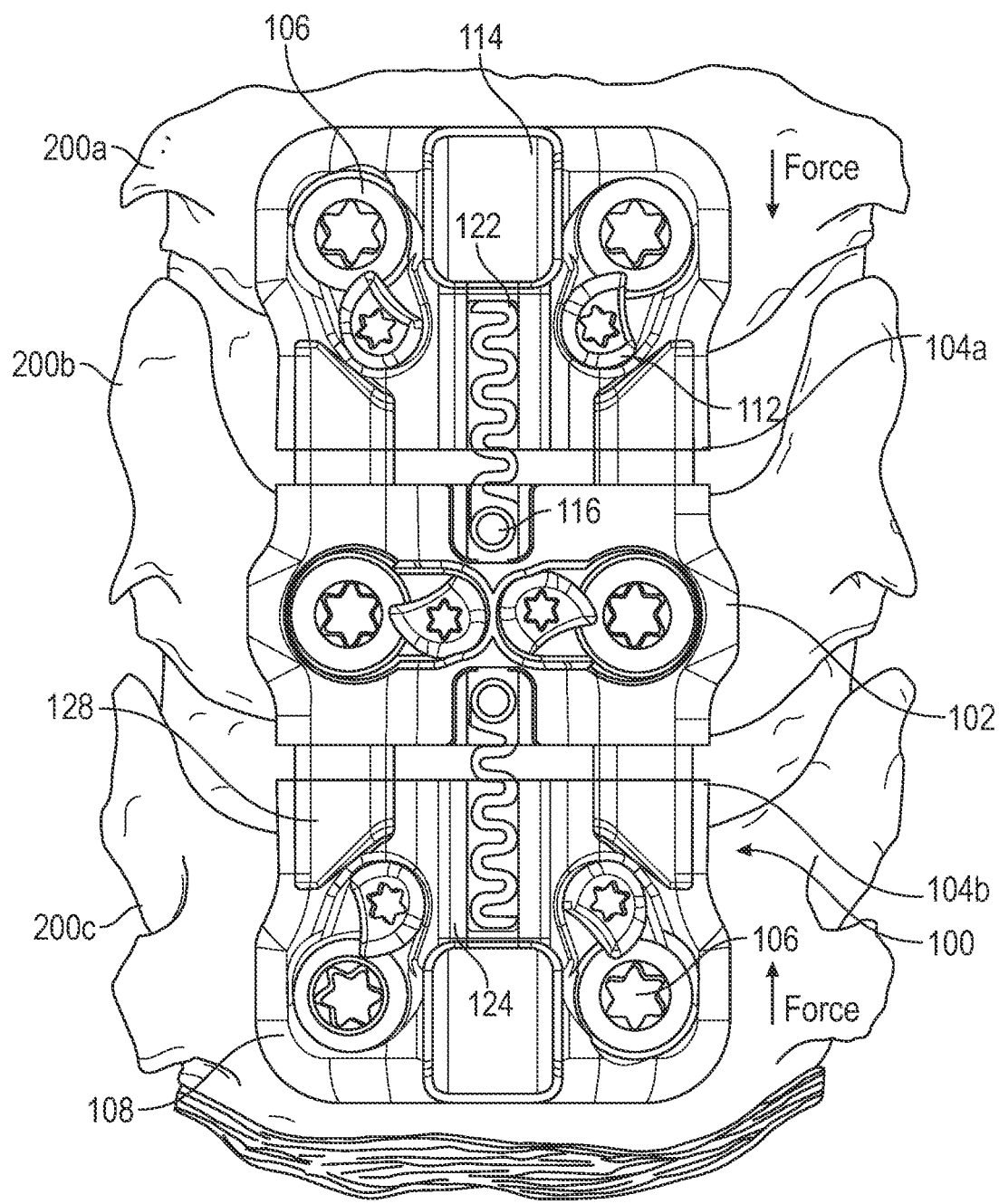
FIG. 7B depicts an exemplary top view of some embodiments of a compression plate following attachment to a vertebral segment with some portions ghosted for viewing purposes.

FIGS. 7A-7B depict exemplary applications of embodiments of compression plate 100. FIG. 7A depicts some embodiments of compression plate 100 attached to vertebrae. FIG. 7B is similar to FIG. 7A with some components ghosted to provide visual depiction of internal components such as spring 122, spring retaining member 124, and one or more connectors 128. Accordingly, FIGS. 7A-7B are best viewed together for the following description.

In some embodiments, locking bone screw 108 is fastened to compression plate 100 prior to compression plate 100 being fastened to a surface. For example, as discussed above with respect to FIG. 1A, locking bone screw 108 may be secured within the corresponding aperture prior to attachment of compression plate 100 to a surface. In other embodiments, locking bone screw 108 is screwed into and secured within the corresponding threaded aperture contemporaneously with attachment of compression plate 100 to a surface. For example, as discussed above the threading of threaded locking bone screw head 120 may not align with the threading disposed within the corresponding aperture. Accordingly, threaded locking bone screw head 120 may be cold-welded to the corresponding aperture as locking bone screw 108 is rotatably attached to the surface (e.g., third vertebra 200c).

As stated above, compression plate 100 may be beneficial in various spinal applications. For instance, compression plate 100 may be beneficial when used as a cervical plate, as illustrated in FIGS. 7A-8B. In some embodiments, first plate segment 104a may be attached to first vertebra 200a, intermediate plate segment 102 may be attached to second vertebra 200b, and second plate segment 104b may be attached to third vertebra 200c. In some embodiments and as described above, greater or less intermediate plates and/or plate segments may be attached to greater or less vertebrae.

During attachment of compression plate 100 to the two or more vertebrae, the associated one or more bone screws 106 may be rotatably attached to the corresponding vertebra. In some embodiments, one or more bone screws 106 may be attached sequentially to the corresponding vertebra. In some embodiments, multiple screws of the one or more bone screws 106 may be rotatably attached simultaneously. In some embodiments, following attachment of one or more bone screws 106 to the corresponding vertebra, one or more locking screw heads 112 may be actuated to prevent backout of any of one or more bone screws 106, as described above with reference to FIGS. 2A-2B. For example, as depicted in FIG. 7A, one or more locking screw heads 112 may be rotated such that protrusions 136 of locking screw head 112 extends outwardly over bone screw head 118. In some embodiments, one or more locking screw heads 112 may be locked or otherwise retained in this position.

When two or more vertebrae flex apart (e.g., the intervertebral distance increases), spring 122 is compressed within spring channel 134 by the movement of spring biasing pin 116 away from intermediate plate segment 102. As discussed above, such movement increases the force exerted by spring 122 on intermediate plate segment 102 and first plate segment 104a or second plate segment 104b. By increasing the force exerted by spring 122 on the various plates, the segments of compression plate 100 (e.g., first plate segment 104a and intermediate plate segment 102) are actively compressed together, and thus the attached vertebrae (e.g., first vertebra 200a and second vertebra 200b) are biased together. Put another way, the spring 122 biases the spring biasing pin 116, thereby applying a force that continuously pushes the first and second segments 104a,b of compression plate 100 to intermediate plate segment 102 throughout the entire range of travel of the first and second plate segments 104a,b. The range of travel of the first and second plate segments 104a,b is defined by the distance of the segments from the intermediate plate segment 102. The spring 122 continues to apply a force to push the first and second segments 104a,b to the intermediate plate segment 102 when the first and second segments 104a,b contact the intermediate plate segment 102. Such active compression provided by compression plate 100 allows for dynamic spinal movement that would be otherwise absent in a rigid cervical plate.

Figure 8B:
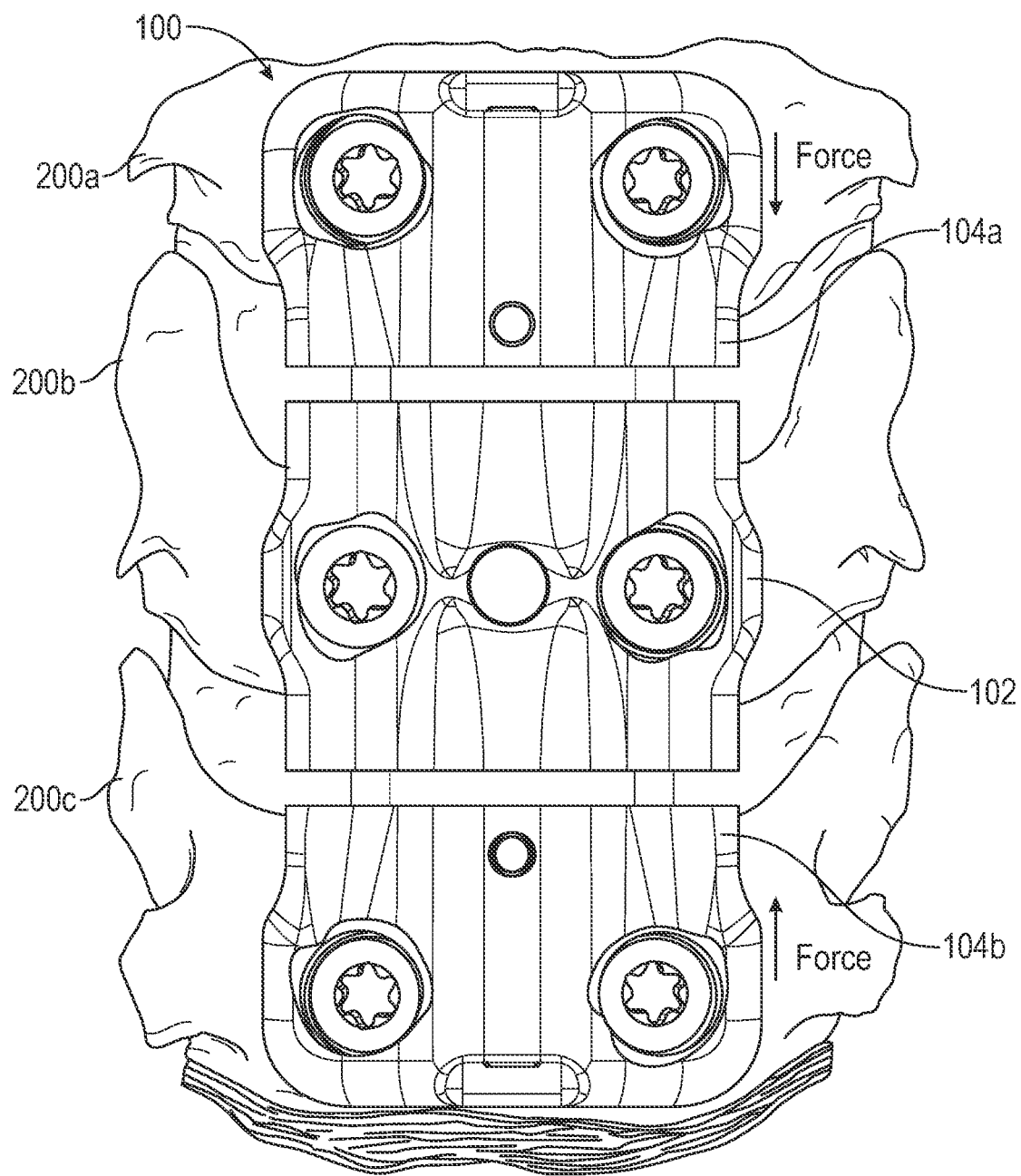
FIG. 8B depicts an exemplary top view of some embodiments of a compression plate in a closed position following attachment to a vertebral segment.

FIG. 8A depicts some embodiments of compression plate 100 attached to vertebrae and utilizing retaining clip 140. FIG. 8B depicts some embodiments of compression plate 100 attached to vertebrae following removal of retaining clip 140. Turning first to FIG. 8A, compression plate 100 is retained in an open configuration by retaining clip 140. As discussed above with respect to FIGS. 4-6, retaining clip 140 may allow for a particular width to be maintained between intermediate plate segment 102 and first and second plate segments 104a, 104b, during installation. In some embodiments, the distance between segments of compression plate 100, as retained by retaining clip 140, may aid in attachment of compression plate 100 to the vertebrae by mimicking the intervertebral space. In some embodiments, the distance between segments of compression plate 100, as retained by retaining clip 140, may mimic the distance between vertebrae having an interbody cage implanted therebetween. In some embodiments, the distance between segments of compression plate 100, as retained by retaining clip 140, may allow for injection of one or more materials between the corresponding intervertebral space. As best illustrated by comparing FIG. 8A to FIG. 8B, in some embodiments the distance between segments of compression plate 100, as retained by retaining clip 140, may allow for increased compressive forces to be applied to the corresponding vertebrae following removal of retaining clip 140.

Turning now to FIG. 8B, some embodiments of compression plate 100 in a closed configuration are illustrated following the removal of retaining clip 140. As discussed above with respect to FIGS. 4-6, retaining clip 140 may be removed after the attachment of one or more bone screws 106 and/or locking bone screw 108 to the vertebrae. As also discussed above, by installing compression plate 100 with spring 122 compressed within spring channel 134, spring 122 will exert greater compressive forces between segments (e.g., first plate segment 104a and intermediate plate segment 102) of compression plate 100 while in the closed configuration than would be exerted by attaching compression plate 100 without compressing spring 122 (i.e., attaching compression plate 100 to vertebrae while in the closed configuration, such as illustrated in FIG. 7A). Accordingly, following removal of retaining clip 140, compression plate 100 provides active compression between first vertebra 200a and second vertebra 200b, as well as between second vertebra 200b and third vertebra 200c.

Features described above as well as those claimed below may be combined in various ways without departing from the scope hereof. The following examples illustrate some possible, non-limiting combinations:

(A1) A compression plate configured to provide an active compression of two or more osseous structures, the compression plate comprising: a plug plate segment comprising a spring retaining member extending therefrom; a socket plate segment moveably coupled to the plug plate segment and receiving the spring retaining member therein; a plurality of bone screws configured to secure the compression plate to the two or more osseous structures, wherein each of the plug plate segment and the socket plate segment includes at least one bone screw of the plurality of bone screws; and a spring disposed at the spring retaining member, wherein the spring is arranged to bias the socket plate segment towards the plug plate segment and thereby provide the active compression between the two or more osseous structures.

(A2) For the compression plate denoted as (A1), wherein the plurality of bone screws includes a locking bone screw configured to couple to the compression plate upon driving the locking bone screw into one of the two or more osseous structures.

(A3) For the compression plate denoted as (A1) or (A2), wherein the locking bone screw comprises a threaded head having threads in a first direction, and wherein an aperture disposed at the compression plate and receiving the locking bone screw has threads in a second direction, the first direction and the second direction being unaligned.

(A4) For the compression plate denoted as any of (A1) through (A3), further comprising: one or more locking screw heads disposed at each of the plurality of bone screws, wherein the one or more locking screw heads are arranged to prevent backout of the plurality of bone screws once driven into the two or more osseous structures.

(A5) For the compression plate denoted as any of (A1) through (A4), further comprising: at least one connector extending from the plug plate segment; and at least one connector recess disposed at the socket plate segment, the at least one connector recess receiving the at least one connector.

(A6) For the compression plate denoted as any of (A1) through (A5), wherein the spring comprises nitinol.

(B1) A spinal compression plate configured to transition between an open configuration and a closed configuration, the spinal compression plate comprising: a plurality of plate segments including at least a first plate segment and a second plate segment; a spring retaining member extending from the first plate segment and defining a spring channel therein; a spring retaining member recess defined by the second plate segment and receiving the spring retaining member therein, a spring biasing pin disposed at the second plate segment and extending through the spring channel, the spring biasing pin movably coupling the second plate segment to the first plate segment; and a spring disposed within the spring channel and engaging the spring biasing pin, wherein the spring biases the spring biasing pin and the second plate segment towards the first plate segment, thereby biasing the spinal compression plate towards the closed configuration.

(B2) For spinal compression plate denoted as (B1), further comprising: a retaining clip configured to retain the spinal compression plate in the open configuration.

(B3) For spinal compression plate denoted as (B1) or (B2), wherein the first plate segment comprises one or more connectors, wherein the one or more connectors are received within one or more first connector recesses at the second plate segment.

(B4) For spinal compression plate denoted as any of (B1) through (B3), wherein the spring is partially compressed when the spinal compression plate is in the closed configuration.

(B5) For spinal compression plate denoted as any of (B1) through (B4), further comprising: a plurality of bone screws extending from each of the first plate segment and the second plate segment, the plurality of bone screws arranged to secure the spinal compression plate to two or more vertebrae.

(B6) For spinal compression plate denoted as any of (B1) through (B5), wherein at least one bone screw of the plurality of bone screws comprises a locking bone screw configured to couple to the spinal compression plate once secured a vertebra.

(B7) For spinal compression plate denoted as any of (B1) through (B6), further comprising: one or more locking screw heads disposed at each of the plurality of bone screws, wherein the one or more locking screw heads are arranged to prevent backout of the plurality of bone screws once driven into the two or more vertebrae.

(B8) For spinal compression plate denoted as any of (B1) through (B7), wherein each of the one or more locking screw heads comprise a protrusion configured to rotatably extend over each of the plurality of bone screws.

(C1) A spinal compression plate configured to provide active compression between two or more vertebrae, comprising: an intermediate segment comprising a first spring retaining member and a second spring retaining member extending therefrom; a first plate segment receiving the first spring retaining member therein, wherein the first plate segment is translatable about the first spring retaining member; a second plate segment receiving the second spring retaining member therein, wherein the second plate segment is translatable about the second spring retaining member; a first spring housed within the first spring retaining member; and a second spring housed within the second spring retaining member, wherein the first spring biases the first plate segment towards the intermediate segment, wherein the second spring biases the second plate segment towards the intermediate segment.

(C2) For spinal compression plate denoted as (C1), wherein the spinal compression plate is configured to transition between an open configuration and a closed configuration, wherein the first plate segment and the second plate segment abut the intermediate segment in the closed configuration.

(C3) For spinal compression plate denoted as (C1) or (C2), wherein each of the first spring and the second spring are partially compressed when the spinal compression plate is in the closed configuration.

(C4) For spinal compression plate denoted as any of (C1) through (C3), further comprising: a removable retaining clip comprising a first clip arm and a second clip arm extending therefrom and configured to retain the spinal compression plate in the open configuration, wherein the first clip arm is disposed between the first plate segment and the intermediate segment, wherein the second clip arm is disposed between the second plate segment and the intermediate segment.

(C5) For spinal compression plate denoted as any of (C1) through (C4), further comprising: a plurality of bone screws arranged to secure the spinal compression plate to at least two vertebrae.

(C6) For spinal compression plate denoted as any of (C1) through (C5), wherein the removable retaining clip is configured to be removed after the spinal compression plate is secured to the at least two vertebrae.

Many different arrangements of the various components depicted, as well as components not shown, are possible without departing from the scope of the claims below. Embodiments of the invention have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims. Although the invention has been described with reference to the embodiments illustrated in the attached drawing figures, it is noted that equivalents may be employed and substitutions made herein without departing from the scope of the invention as recited in the claims.

The invention claimed is:

1. A compression plate configured to provide an active compression of two or more osseous structures, the compression plate comprising:
   a plug plate segment comprising a spring retaining member extending therefrom and defining a spring channel;
   a socket plate segment moveably coupled to the plug plate segment and receiving the spring retaining member therein;
   a plurality of bone screws configured to secure the compression plate to the two or more osseous structures, wherein each of the plug plate segment and the socket plate segment includes at least one bone screw of the plurality of bone screws;
   a spring biasing pin disposed at the socket plate segment and extending through the spring channel, the spring biasing pin movably coupling the plug plate segment and the socket plate segment; and
   a spring engaging the spring biasing pin and disposed at the spring channel of the spring retaining member, wherein the spring is arranged to bias the spring biasing pin and the socket plate segment towards the plug plate segment and thereby provide the active compression between the two or more osseous structures.

2. The compression plate of claim 1, wherein the plurality of bone screws includes a locking bone screw configured to couple to the compression plate upon driving the locking bone screw into one of the two or more osseous structures.

3. The compression plate of claim 2, wherein the locking bone screw comprises a threaded head having threads in a first direction, and wherein an aperture disposed at the compression plate and receiving the locking bone screw has threads in a second direction, the first direction and the second direction being unaligned.

4. The compression plate of claim 1, further comprising:
   one or more locking screw heads disposed at each of the plurality of bone screws,
      wherein the one or more locking screw heads are arranged to prevent backout of the plurality of bone screws once driven into the two or more osseous structures.

5. The compression plate of claim 1, further comprising:
   at least one connector extending from the plug plate segment; and
   at least one connector recess disposed at the socket plate segment, the at least one connector recess receiving the at least one connector.

6. The compression plate of claim 1, wherein the spring comprises nitinol.

7. A spinal compression plate configured to transition between an open configuration and a closed configuration, the spinal compression plate comprising:
   a plurality of plate segments including at least a first plate segment and a second plate segment;
   a spring retaining member extending from the first plate segment and defining a spring channel therein;
   a spring retaining member recess defined by the second plate segment and receiving the spring retaining member therein,
   a spring biasing pin disposed at the second plate segment and extending through the spring channel, the spring biasing pin movably coupling the second plate segment to the first plate segment; and
   a spring disposed within the spring channel and engaging the spring biasing pin, wherein the spring biases the spring biasing pin and the second plate segment towards the first plate segment, thereby biasing the spinal compression plate towards the closed configuration.

8. The spinal compression plate of claim 7, further comprising:
a retaining clip configured to retain the spinal compression plate in the open configuration.

9. The spinal compression plate of claim 7, wherein the first plate segment comprises one or more connectors, wherein the one or more connectors are received within one or more first connector recesses at the second plate segment.

10. The spinal compression plate of claim 7, wherein the spring is partially compressed when the spinal compression plate is in the closed configuration.

11. The spinal compression plate of claim 7, further comprising:
a plurality of bone screws extending from each of the first plate segment and the second plate segment, the plurality of bone screws arranged to secure the spinal compression plate to two or more vertebrae.

12. The spinal compression plate of claim 11, wherein at least one bone screw of the plurality of bone screws comprises a locking bone screw configured to couple to the spinal compression plate once secured to a vertebra.

13. The spinal compression plate of claim 12, further comprising:
one or more locking screw heads disposed at each of the plurality of bone screws,
wherein the one or more locking screw heads are arranged to prevent backout of the plurality of bone screws once driven into the two or more vertebrae.

14. The spinal compression plate of claim 13, wherein each of the one or more locking screw heads comprise a protrusion configured to rotatably extend over each of the plurality of bone screws.

15. A spinal compression plate configured to provide active compression between three or more vertebrae, comprising:
an intermediate segment comprising a first spring retaining member and a second spring retaining member extending therefrom;
a first plate segment receiving the first spring retaining member therein,
wherein the first plate segment is translatable about the first spring retaining member;
a second plate segment receiving the second spring retaining member therein,
wherein the second plate segment is translatable about the second spring retaining member,
wherein the spinal compression plate is configured to transition between an open configuration and a closed configuration such that the first plate segment and the second plate segment abut the intermediate segment in the closed configuration;
a first spring housed within the first spring retaining member; and
a second spring housed within the second spring retaining member,
wherein the first spring biases the first plate segment towards the intermediate segment,
wherein the second spring biases the second plate segment towards the intermediate segment,
wherein each of the first spring and the second spring are partially compressed when the spinal compression plate is in the closed configuration.

16. The spinal compression plate of claim 15, further comprising:
a removable retaining clip comprising a first clip arm and a second clip arm extending therefrom and configured to retain the spinal compression plate in the open configuration,
wherein the first clip arm is disposed between the first plate segment and the intermediate segment,
wherein the second clip arm is disposed between the second plate segment and the intermediate segment.

17. The spinal compression plate of claim 16, further comprising:
a plurality of bone screws arranged to secure the spinal compression plate to at least two vertebrae.

18. The spinal compression plate of claim 17, wherein the removable retaining clip is configured to be removed after the spinal compression plate is secured to the at least two vertebrae.

19. The spinal compression plate of claim 15, further comprising:
at least one locking bone screw secured to a vertebra, the at least one locking bone screw resistant to backing out of the vertebra.

20. The spinal compression plate of claim 19, wherein the at least one locking bone screw comprises a thread form different from a threading located in an aperture disposed on the spinal compression plate such that the thread form and the threading prevent the at least one locking bone screw from backing out of the vertebra.

* * * * *